United States Patent [19]

Ryan

[11] Patent Number: 5,059,185

[45] Date of Patent: Oct. 22, 1991

[54] SAFETY NEEDLED MEDICAL DEVICES

[75] Inventor: Dana W. Ryan, Sandy, Utah

[73] Assignee: Ryan Medical, Inc., Brentwood, Tenn.

[21] Appl. No.: 162,569

[22] Filed: Mar. 1, 1988

[51] Int. Cl.$^5$ ............................................. A61M 5/32
[52] U.S. Cl. ................................... 604/198; 604/263; 128/763
[58] Field of Search ............... 604/110, 192, 194, 195, 604/196, 197, 198, 240–243, 263, 111, 181, 188, 187, 188, 199, 211, 212, 214, 216, 232, 234; 128/763, 766, 762, 764, 765, 766, 767, 770

[56] References Cited

U.S. PATENT DOCUMENTS

| | | | |
|---|---|---|---|
| 2,571,653 | 10/1951 | Bastyen | 604/198 |
| 3,073,306 | 1/1963 | Linder | 604/198 |
| 3,469,581 | 9/1969 | Burke | 604/243 |
| 4,356,822 | 11/1982 | Winstead-Hall | 604/198 |
| 4,417,887 | 11/1983 | Koohi | 604/192 |
| 4,425,120 | 1/1984 | Sampson et al. | 604/198 |
| 4,573,976 | 3/1986 | Sampson et al. | 604/263 |
| 4,631,057 | 12/1986 | Mitchell | 604/198 |
| 4,643,199 | 2/1987 | Jennings et al. | 604/198 |
| 4,655,751 | 4/1987 | Harbaugh | 604/198 |
| 4,666,435 | 5/1987 | Bragineti | 604/198 |
| 4,681,567 | 7/1987 | Masters et al. | 604/198 |
| 4,702,738 | 10/1987 | Spencer | 604/198 |
| 4,702,739 | 10/1987 | Milorad | 604/198 |
| 4,723,943 | 2/1988 | Spencer | 604/198 |
| 4,737,144 | 4/1988 | Choksi | 604/198 |
| 4,738,603 | 4/1988 | Boyan | 604/198 |
| 4,747,830 | 5/1988 | Gloyer et al. | 604/110 |
| 4,747,837 | 5/1988 | Hauck | 604/263 |
| 4,788,231 | 7/1988 | Haber et al. | 604/198 |
| 4,790,827 | 12/1988 | Haber et al. | 604/198 |

*Primary Examiner*—Randall L. Green
*Assistant Examiner*—K. M. Reichle
*Attorney, Agent, or Firm*—David P. Gordon

[57] ABSTRACT

Improved shielded medical devices which minimize accidental needlesticks of the skin by an exposed contaminated needle are provided. The medical devices includes a hollow inner tube body having a pair of circumferential grooves on the outside thereof, and a slightly larger diameter hollow shield which is slidable relative to the inner tube. Lugs circumferentially spaced about the rearward end of the shield yieldingly engage the rearward grooves during use of the medical device and thereby permit normal use of an exposed needle. Thereafter the shield may be moved along the axis of the inner tube to a second position wherein the shield covers the now-contaminated needle. A plurality of axial slits in the rearward end of the shield in conjunction with a shoulder on the inner tube body forwardly adjacent a forward circumferential groove permit the medical devices to be assembled. The slits also permit the shield to move along the ramped outer wall of the inner tube during movement of the shield into its shielding position. In the unshielded position of the medical devices, a plurality of teeth on the forward end of the inner tube engage notches in the forward end of the outer shield to prevent rotational movement therebetween during use of the medical devices.

19 Claims, 4 Drawing Sheets

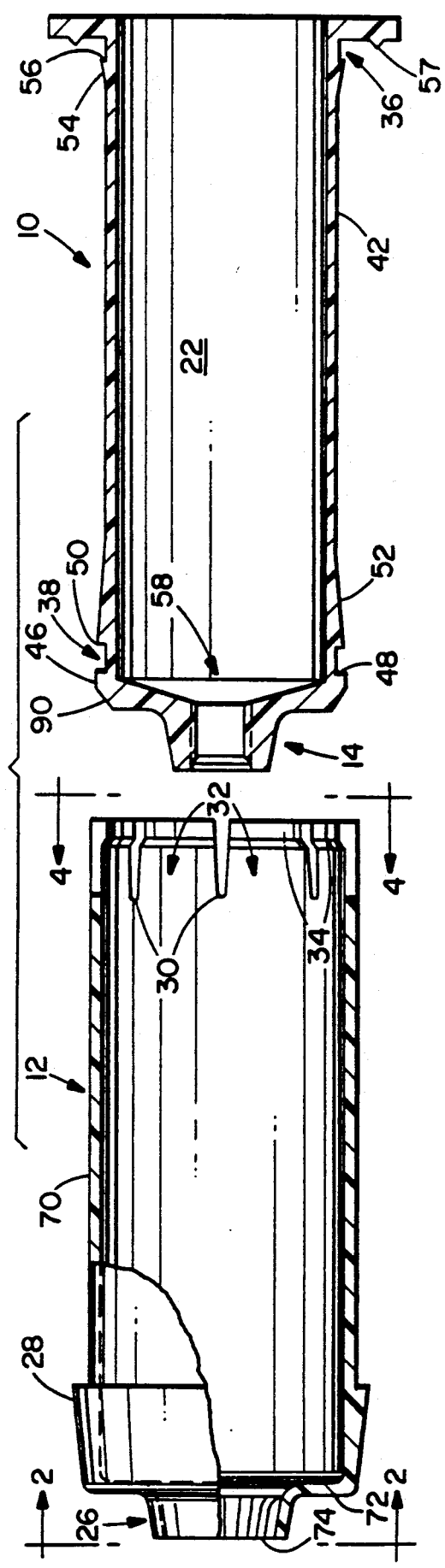
FIG. 1
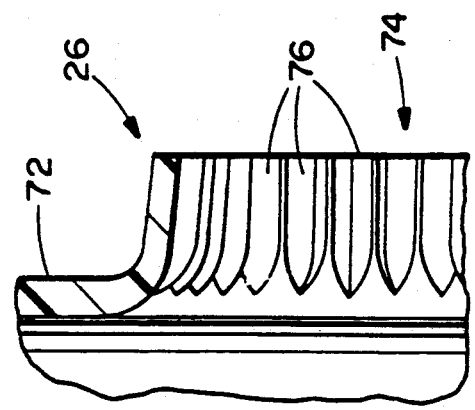
FIG. 3
FIG. 4
FIG. 2

SAFETY NEEDLED MEDICAL DEVICES

BACKGROUND OF THE INVENTION

The present invention generally relates to improvements in safety needled medical devices which are designed to minimize the incidence of accidental pricking of the skin and resulting spread of infectious diseases by an exposed contaminated needle after use thereof. The disclosed devices may be used as blood collection tube holders, syringes with or without an attached needle, and prefilled syringes.

Accidental needlesticks have long been a problem in the medical profession. Accidental needlesticks most often occur during the recapping of a contaminated needle or immediately after use and prior to safe disposal. Such needlesticks place the medical professional (clinician) at risk. When needles are not recapped, additional accidental needlesticks are caused by uncapped needles found in patient beds, linens, and in garbage cans, and place health care house keeping and sanitation personnel at risk. Because accidental needlesticks can now result in deadly incurable diseases as well as the previously appreciated serious, but curable diseases, the need for eliminating the needlestick problem has reached extreme urgency. In addressing the urgency, many devices have been proposed. Indeed, the prior art discloses a number of devices which are arranged to shield the needle of the device after use, but none are as simple to manufacture, assemble, and use as the devices of the present invention A benefit of the devices of the present invention is that the devices require no change in the method of use or technique by medical personnel, i.e. the medical practioners will use the devices in the same way they previously used standard hypodermic syringes, IV catheters, and blood collection tube holders, except that after use they will move a shield to cover the exposed contaminated needle in a very easy, simple and straightforward manner.

Included in the prior art among many safety devices are safety-needled syringes such as are disclosed in U.S. Pat. Nos. 2,571,653 to Bastien, 4,026,287 to Haller, 4,425,120 to Sampson et al., 4,573,976 to Sampson et al., 4,631,057 to Mitchell, et al. 4,643,199 to Jennings, Jr. et al., 4,655,751 to Harbaugh, 4,666,435 to Braginetz, 4,681,567 to Masters et al. None of these devices, however, have gained acceptance due to the fact that they require many complex pieces and thus become expensive to manufacture and assemble, and/or because in utilizing the devices, they require the clinician's procedure and technique to change. For example, in U.S. Pat. No. 4,425,120 to Sampson et al., a complex arrangement of tracks including axial and circumferential components of shield and syringe members are required, making manufacture and assembly more difficult and expensive. Also, in use, the clinician must rotate the shield relative to the syringe tube and force the track engaging member of the syringe through a restriction in the circumferential portion of the track in the shield to lock the shield relative to the syringe tube. The U.S. Pat. No. 4,631,057 to Mitchell requires a collar member over which a shield slides. The device is complex, difficult to manufacture and assemble, and requires permanent attachment of the collar to the syringe tube. The U.S. Pat. No. 4,573,976 to Sampson et al., requires additional intricate members which are attached to both the tube and the shield and which provide a locking action. The additional members are expensive to manufacture and assemble, unwieldy to handle, and would require a clinician to develop a new technique for utilization.

U.S. Pat. No. 4,655,751 to Harbaugh requires at least one slide groove to maintain the shield in the proper rotational axis and to thereby align a pair of ears on the shield with either one of two pairs of pockets in the outer surface of the syringe tube. Besides being relatively expensive to manufacture and assemble due to the ears and pockets, it also requires flexing of the shield to move it to the needle-shielding position, and thus has the potential for cracking or breaking. Similarly, U.S. Pat. No. 4,681,567 to Masters et al., requires a slide grooves in a shield and knobs or ears on the tube. Restrictions in the groove provide locking positions for the shield. Again, however, the knobs may be costly to manufacture and assemble and are prone to breaking. Also, it is not evident how such a device could be manufactured without sonically welding the shield around the tube, as any attempt to slide the shield over the tube and into a non-extended position would require overcoming the same locking action which is used to finally lock the shield relative to the tube.

U.S. Pat. No. 4,666,435 to Braginetz requires a complex and difficult to manufacture arrangement of tracks, rails, detents and stop surfaces, and would be much more expensive to make and assemble than the present invention Further, to lock the syringe tube and shield, the user must step through a predetermined sequence of relative rotational and longitudinal movements between the shield and the syringe tube. U.S. Pat. No. 2,571,653 to Bastien is simpler in design and has a single latch secured by a tensioning device to lock the shield at fixed points on the syringe tube, but the shield would not be as secure in its position covering the needle due to the single latch, and any mishandling of the device could cause movement of the tensioning device and exposure of the needle.

Finally, U.S. Pat. No. 4,026,287 to Haller and No. 4,643,199 to Jennings, Jr. show safety devices which utilize a technique of withdrawing the needle into the tube in order to render the needle harmless. These devices, and others like these typically require additional parts and are difficult to manipulate.

SUMMARY OF THE INVENTION

It is therefore an object of the present invention to provide improved shielded medical devices which are easy and economical to manufacture and assemble, and which do not require change of technique and procedure to use.

A further object of the present invention is to provide improved shielded medical blood collection tube holders, and syringes of different kinds with standardized locking mechanisms in which movement of the shield from the unshielded position to the locked shielded position may be accomplished in an easy, uniform sliding motion.

Another object of the invention is to provide economical improved shielded medical devices utilizing a shield which provides a positive indication when locking into a shielded position.

Yet another object of the present invention is to provide improved shielded medical devices in which rotation of the shield relative to an inner tube body is prevented when the medical device is in use.

The improved safety needled medical devices of the present invention achieve the above-listed objects as hereinafter disclosed. The devices, whether for use with syringes or blood collection tube holders, are comprised of two parts. A first part is a hollow cylindrical inner tube body which is adapted to have mounted at its forward end a standard hollow needle, and to receive a standard plunger or vacuum blood collection tube through its open rearward end. The outside of the inner tube body (hereinafter referred to as the "tube", or the "inner tube") is configured with a pair of axially spaced circumferential grooves with one of the grooves preferably being formed towards the rearmost end of the tube adjacent an outward extending finger positioning flange, and the other of the grooves preferably being near the forward end of the tube. The second part of the safety needled devices is an outer safety shield. The outer safety shield (hereinafter referred to as the "shield", or the "outer shield") is of slightly larger diameter than the inner tube and is assembled over the tube. The outer shield is arranged to be slidable relative to the inner tube, and has a plurality of slits in the rearward end thereof, the slits being coaxial with the long axis of the outer shield and inner tube. An inward circumferential protrusion which is cut by the coaxial slits provide inwardly extending lugs which are circumferentially spaced about the rearward end of the shield. The lugs yieldingly engage the rearmost groove thereby allowing the needle to be exposed and permitting normal use of the medical device. Thereafter, partially due to the flexible tabs produced by the plurality of slits at the rearmost end of the shield, the shield may be moved forward from the rearmost groove to a needle shielding position where the lugs engage the forward groove. The shield then prevents accidental contact with the contaminated needle. Rachet, or other similar means connected with the inner tube and the outer shield are provided to prevent rotation of the outer shield relative to the inner tube when the shield is in its retracted position and the needle is exposed.

A better understanding of the improved safety needle medical devices of the present invention, and additional advantages and objects of the invention will become apparent to those skilled in the art upon reference to the detailed description and accompanying drawings.

BRIEF DESCRIPTION OF DRAWINGS

FIG. 1 is a plan view showing the standardized locking mechanism of the inner tube and outer shield of the invention prior to assembly as a medical safety-needled device;

FIG. 2 is an end view of the outer shield of FIG. 1, taken along line 2—2 of FIG. 1, and showing a ratchet mechanism;

FIG. 3 is a side view of the ratchet mechanism of the outer shield shown in FIG. 1;

FIG. 4 is an end view of the outer shield taken along line 4—4 of FIG. 1;

DETAILED DESCRIPTION OF THE PREFERRED EMBODIMENTS

Figure 5A:
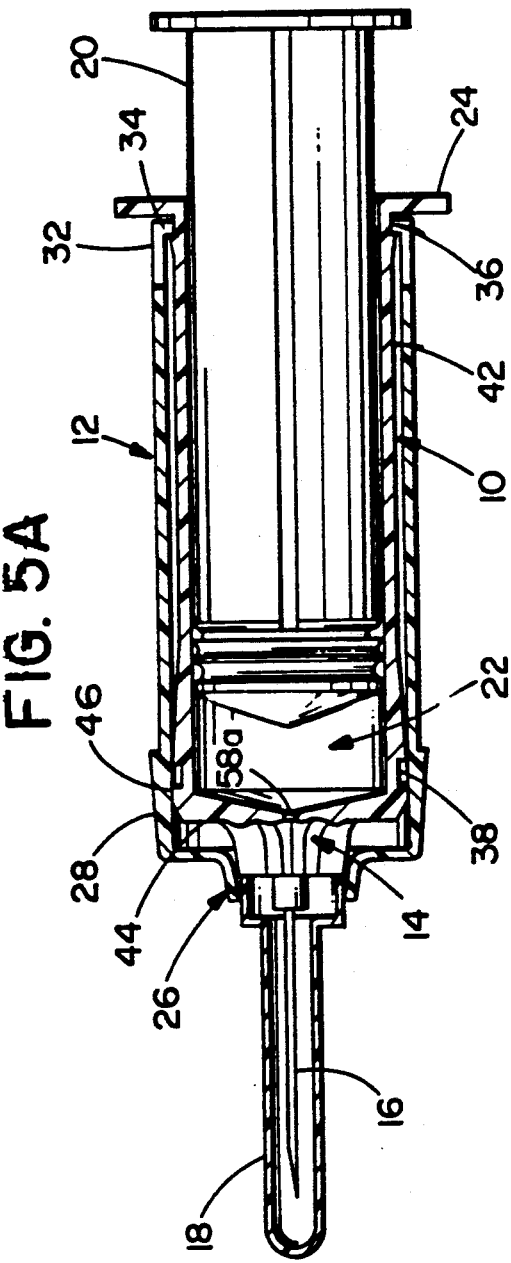
FIG. 5a is a longitudinal sectional view of the syringe embodiment of the safety-needled invention where the outer shield is in a retracted position relative to the inner tube so that the needle is unshielded and ready for use.
Figure 5B:
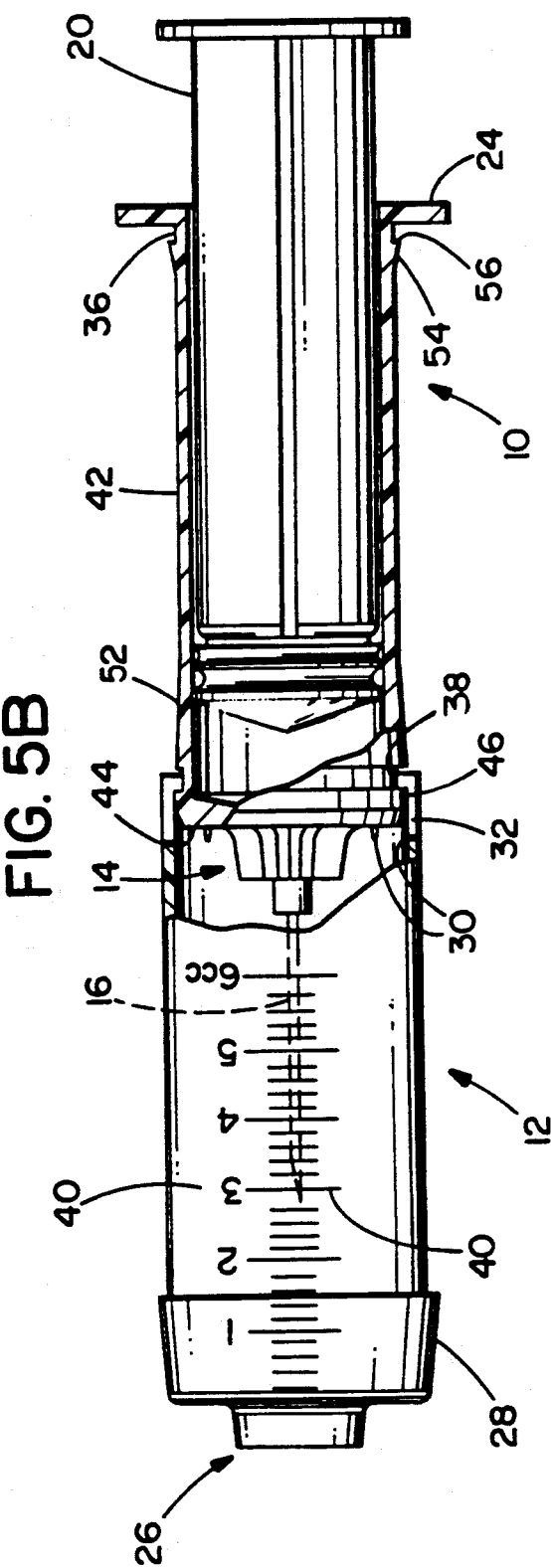
FIG. 5b is a longitudinal sectional view of the syringe embodiment of the safety needled invention where the outer shield is in an extended position relative to the inner tube so that the contaminated needle is shielded.
Figure 7:
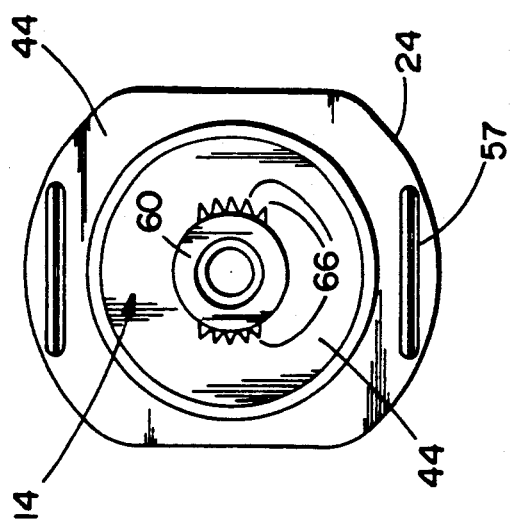
FIG. 7 is an end view of the inner tube of FIG. 6, taken along line 7—7 of FIG. 6.
Figure 6:
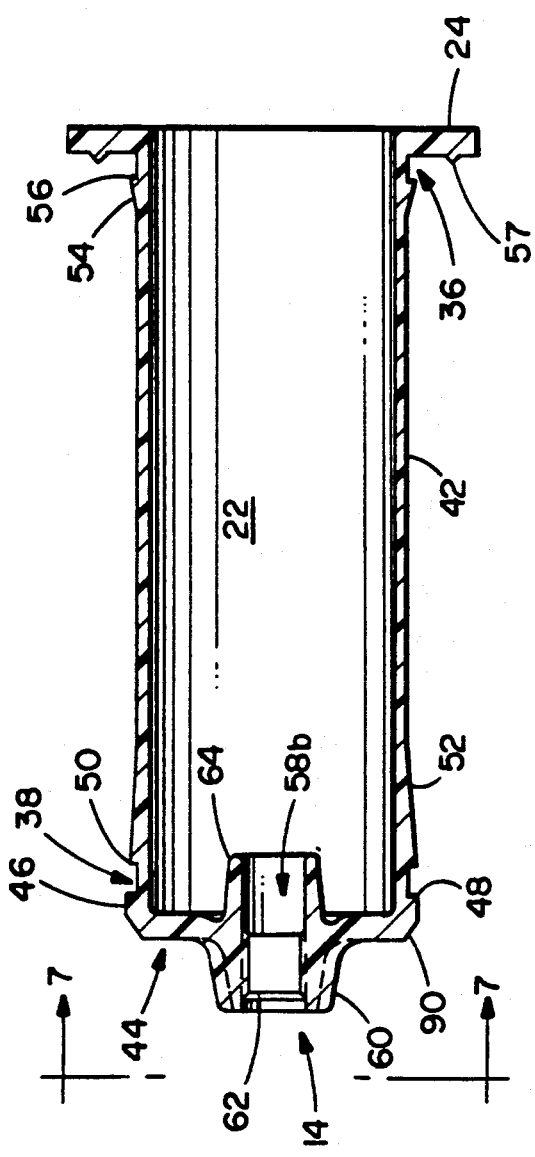
FIG. 6 is a longitudinal sectional view of the inner tube of a blood collection tube holder embodiment of the invention.
Figure 8:
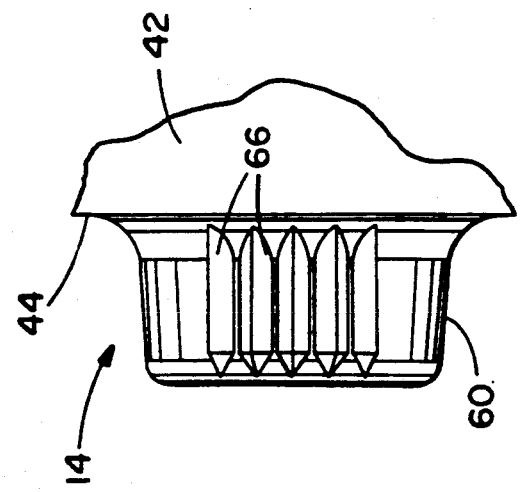
FIG. 8 is a side view of the inner tube ratchet means shown in FIG. 6.

FIGS. 1-4 show the basic structure of the improved safety-needled device of the invention, with FIG. 5a showing the syringe embodiment with the needle exposed and ready for use, and FIG. 5b showing the syringe embodiment after use with the outer shield in its forwardmost position in which the needle is covered, FIGS. 6-8 showing the blood collection tube holder of the invention, and FIG. 9 showing the prefilled syringe embodiment of the invention.

Referring to FIGS. 1-4, the improved safety medical device comprises two generally cylindrical pieces, a hollow inner tube 10 and an outer shield 12, both pieces typically being made of molded plastic or other acceptable material. Molded into the forward end of the outer surface of inner tube 10 is a rachet assembly 14 including locking teeth which are shown in detail in FIGS. 7 and 8 with reference to the blood collection tube holder embodiment. The inner surface of the forward end of inner tube 10 is also adapted to securely mate typically with a threaded structure to hold a standard hollow needle 16 shown with a removable needle cover 18 thereon Inner tube 10 is further provided with a cavity 22 into which drugs, pharmaceuticals, blood or other fluids may be aspirated and then forced through needle 16 into a body, or into which a blood collection tube may be placed so that blood from the body may be drawn. A flange 24 is molded at the rearward end of inner tube 10 to act as a finger support while forcing the contents in the cavity into the body, or while withdrawing the needle from the patient, pharmaceutical vial, or other container.

One important aspect of the invention is the precise geometry of the outer wall 42 of the inner tube 10. Circumferential grooves 36 and 38 are formed in wall 42. An end wall 44 extends from the forwardmost end of wall 42 and supports ratchet assembly 14 which is integral therewith and is described in more detail hereinafter with respect to the blood collection tube holder embodiment shown in FIGS. 6-8. At the junction of end wall 44 and wall 42 a shoulder 46 is formed, the rearward extension of shoulder 46 forming the forwardmost ledge 48 of circumferential groove 38. The rearmost ledge 50 of groove 38 has a slightly smaller diameter than that of shoulder 46, and as wall 42 extends rearward from ledge 50, its outside diameter gradually decreases to form a sloped wall portion or ramp generally illustrated by 52. Thereafter, the wall 42 is of constant diameter until it reaches slightly raised shoulder 54 which forms the forwardmost ledge 56 of circumferential groove 36. The forwardmost portion of flange 24 forms the rearwardmost ledge of groove 36, and flange 24 has tine 57 for added finger support. The advantages of the entire construction will be described hereinafter. It should be understood at this juncture, however, that the inner tube 10 is a single, preferably molded, integral unit.

The outer shield 12 has an inside diameter which is slightly larger than the outer diameter of the inner tube 10. The outer shield 12 is adapted to fit over inner tube 10 and to be slidable between a rearward position and a forward position (as respectively shown in FIGS. 5a and 5b for the syringe embodiment). The outer shield 12 has a locking nozzle or ratchet means 26 molded into its inner surface at the forward end thereof, the locking nozzle including a plurality of locking notches, shown particularly in FIGS. 2 and 3. Locking nozzle 26 is preferably annular in shape and is connected to the outer cylindrical wall 70 of shield 12 by end wall 72. A substantially annular opening 74 at the center of locking nozzle 26 is adapted to permit a standard needle 16 to extend therethrough when the shield 12 is in its closed position. As will be described, the locking nozzle 26 engages the locking teeth in the rachet assembly 14 when the shield 12 is in its rearward (retracted) position, thereby preventing rotation of the outer shield 12 relative to the inner tube 10 during an injection or phlebotomy.

A flanged safety ridge 28 is formed near the forward end of outer shield 12 to assist the user in grasping the shield 12 and slidably moving it from its retracted position to its extended and locked position. The shield 12 also has at its rearmost end a plurality of circumferentially spaced axial slots 30 which form there-between tabs 32, the tabs 32 being slightly flexible. Formed on the inner surface of tabs 32 are a plurality of protrusions or lug members 34 (seen in FIG. 4) which are adapted to yieldingly engage a circumferential groove 36 preferably located at the rear end of inner tube 10 to thereby maintain the shield 12 in its retracted position (shown in FIG. 5a with respect to the syringe embodiment). The tabs 32 are sufficiently flexible to permit the lug members 34 to be forced out of groove 36, and to permit the shield 12 to be moved forward manually to its extended or locked position (shown in FIG. 5b with respect to the syringe embodiment) in which the lug members 34 engage a second circumferential groove 38. As will be described hereinafter, the construction of the shield 12 and inner tube 10 are such that the shield 12, when in the extended locked position with lug members 34 locked into groove 38, is extremely difficult to remove from the inner tube 10, while during assembly, the shield 12 is slipped over tube 10 without lug members 34 locking into groove 38.

As aforementioned, a plurality of notches or grooves 76, shown in FIGS. 2 and 3, are formed on the inside wall of locking nozzle 26. The notches 76 are designed and sized to mesh with the raised teeth 66 (seen in FIG. 7) extending from the outside of wall 60 of ratchet assembly 14 when shield 12 is positioned as shown in FIG. 5a with respect to the syringe embodiment. The meshing of the teeth 66 and notches 76 prevents rotation of shield 12 relative to inner tube 10 which could be distracting to the medical personnel using the medical device. While twenty-four notches 76 are shown extending completely about the inside wall of locking nozzle 26, the exact number and shape may be varied and will be dependent on the size, shape and location of raised teeth 66. With raised teeth 66 on opposite sides of wall 60, the teeth 66 will mesh with notches 76 regardless of the relative circumferential alignment between inner tube 10 an outer shield 12.

Another important feature of the invention is the plurality of forwardly extending slits 30 in the rearward portion of wall 70 of shield 12. As shown, eight such slits 30 are provided, although the exact number will depend on the size of the shield 12 and the flexibility of the plastic or other acceptable material from which it is constructed As seen in FIGS. 1 and 4, the slits 30 in the shield wall form slightly flexible tab-like members 32 at the rear end of the shield. As seen best in FIG. 4, a plurality of lug members or protrusions 34 extend radially inwardly from each of the tabs 32, and also extend circumferentially along each tab 32. Lug members 34 are adapted to fit within and lockingly engage circumferential grooves 36 and 38 of inner tube 10. The flexibility of tab 32 and their corresponding lug members 34 provide advantages in assembling the shielded medical device, and in moving the shield 12 from its unshielded (open) to its shielded (closed) position. The precise size and shape of lug members 34 may be changed to suit the particular situation.

Turning to FIGS. 5a and 5b, the safety-needled syringe embodiment of the invention is shown, with like numbers indicating like parts. In FIG. 5a, the outer shield 12 is in its retracted position relative to the inner syringe tube 10 such that needle 16 is unshielded Ratchet means 14 of the syringe tube 10, and locking nozzle 26 of the outer shield 12 are engaged to prevent rotation of the shield relative to the inner syringe tube 10, while lug member 34 of tabs 32 are seated in 3 circumferential groove 36. As shown in FIGS. 5a and 5b, the inside of inner syringe tube 10 as arranged to be generally cylindrical in shape, and at its forward end is shaped to accommodate the typically rubber end of a standard plunger 20. Thus, chamber 22 of the syringe tube 10 is shown accepting plunger 20 which will either force the contents of chamber 22 through a small annular opening 58a in the ratchet assembly 14 and into and through the needle 16, or aspirate a fluid through the needle 16, the small annular opening 58a in the ratchet assembly, and into the chamber 22. As seen in FIG. 5b, graduated markings 40 typically in cc measurements are placed on shield 12 for clear visibility, although since shield 12 is preferably transparent, the markings 40 may be placed on the syringe tube 10.

After injection, the rubber end of plunger 20 is seated at the accommodating front end of the chamber 22. By applying some force to the shield 12, shield 12 is moved to the position indicated in FIG. 5b such that lugs 34 are seated in circumferential groove 38, and the needle 16 is shielded by shield 12. Shoulder 46 and ledge 50 of the syringe tube 10 keep the lugs 34 of shield 12 firmly in place so that shield 12 cannot accidentally retract or fall off of the syringe tube 10 and thereby reexpose the contaminated needle It is of note with respect to FIGS. 5a and 5b, that the front end of the shield 12 extends further than is shown in FIG. 1 so that the ratchet means 26 of the shield 12 can properly engage ratchet means 14 of the syringe tube 10. Thus, while the shield 12 is essentially identical for all of the medical devices of the invention, its exact length and shape at the front end is dependent on the device with which it is to engage so as to prevent rotation.

Turning to FIGS. 6-8, the inner tube 10 of the blood collection tube bolder embodiment of the invention is provided. As is seen in FIG. 7, rachet assembly 14 has an annular opening 58b at the center thereof. Also, as seen in FIG. 6, the ratchet 14 assembly of inner tube 10 of the blood collection tube holder has a cylindrical forwardly extending wall 60 which is provided at the inside circumference thereof with threads 62 or other means by which a standard hollow needle may be attached and communicate through annular opening 58b with cavity 22. For the blood collection tube holder device, inner tube 10 is also provided with a rearwardly extending cylindrical wall 64 may be shaped to receive the forward end of a vacuum blood collection vial (not shown) in sealing engagement therebetween. It should be appreciated that in the blood collection tube holder embodiment, the flange 28 on the outer shield 12 not only provides a safety ridge for grasping and pushing shield 12, but may be used as a vacuum vial penetration indicator line. Thus, the self-sealing rubber end of the vacuum vial may be axially inserted up until that point without the back point of the standard phlebotomy needle puncturing the same.

As aforementioned, the rachet assembly 14 of the inner tube 10 includes a plurality of raised teeth 66, which as seen in FIGS. 7 and 8 extend outwardly from the outside surface of wall 60 of rachet assembly 14. Five teeth 66 are shown on diametrically opposed sides of wall 60, but the exact number and exact location of the teeth 66 may be varied. The teeth 66, as was aforedescribed, mesh with notches 76 of in the locking nozzle 26 of shield 12 to prevent rotation of shield 12 relative to inner tube 10 when the shield is in its retracted position.

Figure 9A:
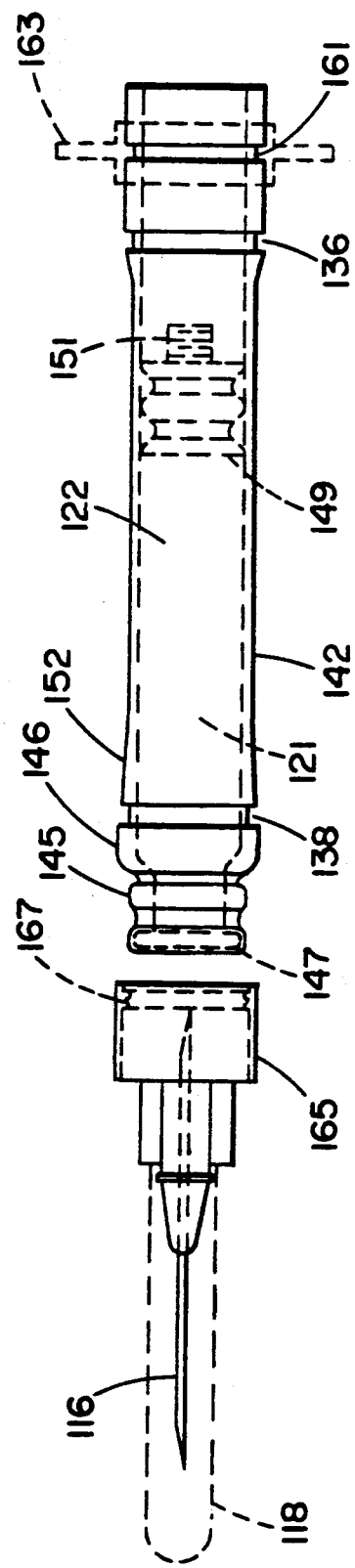
FIG. 9a is plan view of the inner tube for the prefilled syringe embodiment of the safety-needled invention.
Figure 9B:
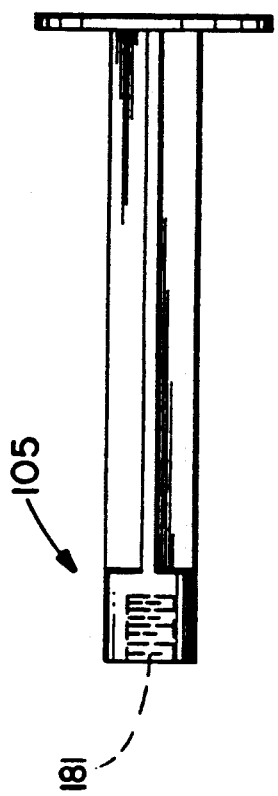
FIG. 9b is a plan view of the plunger arm for a prefilled syringe.

The inner tube 110 of the prefilled safety syringe embodiment of the invention is seen in FIG. 9a, with the disposable plunger arm 105 seen in FIG. 9b. (In this embodiment corresponding elements will have corresponding numbers with the numbers of FIG. 9a being greater by one hundred). The inner tube 110 of FIG. 9a combines many of the standard features of a prefilled syringe with the afore-described inner tube features of the instant safety-needled invention Thus, for purposes of the standard prefilled syringe, the inner tube 110 is preferably made of or lined with glass. The medicated liquid 121 is maintained in chamber 122 which is bounded by the cylindrical wall 142, a shaped metal cap 145 having an hermetic seal 147, and a rubber plunger seal 149 having a male threaded member 151 extending therefrom. Also, for purposes of the standard prefilled syringe, the rear end of the inner tube 110 is provided with a groove 161 for a preferably plastic snap-on flange 163, while the front end metal cap 145 is arranged to mate with a needle hub 165 having a ridge ring 167 on one end for mating with the metal cap 145 , and means for accepting and holding a double pointed needle 116 on the other end. Typically, the needle 116 is provided with a protective cover 118 which must be removed before an injection. A disposable plunger arm 105 seen in FIG. 9b is provided with a female thread member 181 which is screwed onto the male threaded member 151 of the inner tube 110 prior to injection. After mating, force may be applied to the plunger arm 105 so as to force the medicated liquid out through the double pointed needle 116.

As seen in FIG. 9a, the inner tube 110 also includes the safety-needled features. Thus, provided in the outer surface of the inner tube 110 are front and rear grooves 138 and 136 into which the lugs of an outer shield may extend, with front groove 138 being deeper than rear groove 136. Also, preferably, the outer surface of inner tube 110 is provided with a shoulder 146 which prevents the outer shield from leaving the front groove 138, as well as a ramped surface 152 which helps provide the clicking/locking action.

Upon assembly of any of the shielded medical devices, preferably by machine in an automated production, the open end of the outer shield 12 is forced over the shoulder 46 (146) of the inner tube 10 (110), (FIG. 9 numbers not being listed hereafter). The lug members 34 attached to tabs 32 initially contact the sloped wall portion 90 (FIG. 1) and the sloped wall portion 90 forces the flexible tabs 32 outwardly in a fanlike manner. As the lug members 34 pass over and by raised shoulder 46, they instantaneously remain spread, both due to the contraction time required to reassume an unstressed position and due to the position assumed with the tabs angling away from wall 42 of tube 10, such that they can be quickly moved past groove 38 without falling into groove 38. As the shield 12 is pushed rearwardly over the inner tube 10, the lug members 34 press against ramp 52 which is of decreasing diameter, i.e. the tabs 32 are no longer flexed outwardly as a result of the reduced diameter of wall 42, and become parallel. The lug members 34 at the end of the shield 12 ultimately pass over slightly raised shoulder 54, and lug members 34 fall into circumferential groove 36, where the shield 12 is substantially fixed as shown in FIG. 5a.

After the medical device is used and becomes contaminated, the user removes the needle from the patient or other contaminated area and presses forward on safety ridge 28. Because circumferential groove 36 is not as deep as circumferential groove 38, lug members 34 are not deeply seated in circumferential groove 36. Since tabs 32 are slightly flexible, it does not take a great deal of force to push the lugs 34 out of groove 36 and over raised shoulder 54. As the shield 12 is pushed forward, the lug members 34 contact ramp 52 in a direction in which the diameter of the wall 42 is increasing. This provides increased friction and tension on the tabs 32, i.e., the user is aware of the increase in force needed to keep the shield 12 moving forward. The lug members 34 eventually fall into circumferential groove 38 with an audible click, providing a positive indication of locking beyond the visual indication. Because of its depth and because of the increased diameter of raised shoulder 46, groove 38 retains the shield fixed as shown in FIG. 5b. It is difficult to remove the shield once it is locked into circumferential groove 38, and a positive lock is assured, completely protecting medical personnel and others against needlestick injuries from the contaminated needle 16. The shielded medical device is then safely discarded in accord with established procedures.

The shielded safety medical devices of this invention may be used in numerous circumstances and for differing purposes, all of which are within the scope of this invention A common use would be by a phlebotomist (clinician) for obtaining blood samples from a patient. For this usage the phlebotomist (clinician) screws a capped sterile blood collection needle 16 into the threads 62 of inner tube 10. Typically, the phlebotomy needle (not shown) extends a short distance into cavity 22 of the inner tube 10, and a vacuum vial (not shown) having a rubber or plastic stopper is inserted into the tube 10 rather than a plunger. The stopper of the vacuum vial is penetrated by contact with the rearward extension of the needle, and blood is drawn into the vacuum vial through the needle which has been inserted into a vein of the patient. Once the blood sample is taken (if desired, several tubes of blood may be obtained), the needle is removed from the patient, the vacuum vial(s) now filled with a blood sample(s) is removed from the inner tube 10, and the phlebotomist (clinician) then slides the shield 12 over the inner tube 10 until the shield clicks and locks in place, thereby protecting personnel from injury from the contaminated needle or blood. The shielded blood collection tube holder is then safely disposed of, protecting against potential injuries an inadvertent contamination.

When used simply as a syringe, the clinician attaches the appropriate size needle to the syringe tube, removes the end cap and aspirates the required drug, medication, or blood into the syringe. The drug, medication, or other liquid is then administered to the patient directly by injection or through I.V. administration lines. Upon removing the needle from the patient, the safety shield is moved forward until the lugs of the tabs of the outer shield click and lock securely in the forward groove in the syringe tube. With such a procedure, the shield surrounds the needle as shown in FIG. 5b, and the syringe and contaminated needle may then be safely discarded.

Similar procedures are followed with safety syringes with needles already attached, or with pre-filled syringes which ordinarily require loading the syringe into a plunger mechanism in order to administer the drugs, medications, or other fluids contained therein. In either case, the syringe tube and shield of this invention are useful. It is also within the scope of this invention to use its teachings with intravenous catheters.

There has been described and illustrated herein various improved shielded safety medical devices. While particular embodiments of the invention have been described, it is not intended that the invention be limited thereby, as it is intended that the invention be broad in scope. Thus, for example, while the invention was described as comprising essentially two unitary pieces, it will be appreciated that several pieces could be utilized to form either the tube or the shield. Moreover, while the wall of the tube is preferably formed with a ramp to cause the shield to "click" when the lugs of the shield snap into the circumferential groove of the tube, it will be appreciated that the ramp is not essential to the invention. Further, while the locations of the grooves in the inner tube of the embodiments were described as being at the forward and rear ends of the inner tube, those skilled in the art will appreciate that the exact location is not critical provided the contaminated needle is shielded by the shield after use. Thus, if the needle is short relative to the shield, the front groove can be located further back on the inner tube. Without jeopardizing the effectiveness of the device. Likewise, if the inner tube is long relative to the shield, the rear groove can be located away from the rear of the inner tube without the shield interfering with the needle when the shield is in its retracted position. Further yet, while the rear portion of the outer shield was described as having axial "slits", the slits may be thought of as "slots". Thus, for purposes herein, the thickness of those slits or slots is a matter of choice and the terminology is to be read broadly such that slits and slots are equivalent. Therefore, it will be apparent to those skilled in the art that yet other changes and modifications may be made to the invention as described without departing from the scope of the invention as so claimed.

I claim:

1. A medical device for assembly with a hollow needle comprising:
   a) an inner tube member having a substantially cylindrical inner surface, a front end adapted to have the hollow needle secured thereto, an open rear end, and an outer surface having first and second circumferential grooves, said first groove being forward of said second groove, said outer surface having a shoulder adjacently forward of said first groove with said shoulder being slightly larger in diameter than the outer surface of said inner tube member adjacently rearward of said first groove; and
   b) a plastic hollow outer shield member having a substantially cylindrical inner surface with an inner diameter at least equal to the outer diameter of said outer surface of said inner tube member, a front end having an opening therein, a substantially open rear end having a plurality of slots extending forward from said rear end and spaced about said shield member rear end, the portions of said shield member between adjacent slots forming a plurality of slightly flexible tabs, and a plurality of inwardly extending lug members attached to at least some of said tabs, the inner diameter of said lug members being at least as great as the outer diameter of at least most of said outer surface of said inner tube member but less than the outer diameter of said inner tube member adjacently rearward of said first groove, adjacently forward of said second groove, and at said shoulder, said lug members engaging said second circumferential groove to maintain said shield member in a first retracted position in which the hollow needle is exposed, and further fixedly engaging said first circumferential groove to maintain said shield member in a second extended position in which the needle is covered by said shield, wherein said lug members are disengageable from said second circumferential groove and said shield member is slidable between said first position and said second position, and wherein in an assembly mode said lug members engage said shoulder of said outer surface of said inner tube member and flex said tabs outwardly as a result of the engagement, and engage said outer surface of said inner tube rearward of said first groove without fixedly engaging said first circumferential groove in response to a longitudinal axial movement of said shield member relative to said inner tube member in a manner opposite to said sliding of said shield member between said first and second positions.

2. A medical device according to claim 1, wherein:
said slots in said rear end of said shield member are coaxial with the longitudinal axis of said shield member and extend a relatively short distance along said shield member.

3. A medical device according to claim 1, wherein:
said outer surface of said inner tube member is arranged with a first ramp substantially forwardly adjacent said second circumferential groove, said first ramp being of decreasing diameter as it extends forward of said second circumferential groove, and said outer surface of said inner tube member is further arranged with a second ramp substantially rearwardly adjacent said first circumferential groove, said second ramp being of increasing diameter as it extends forward toward said first circumferential groove, wherein said lug members are arranged to slidably engage said outer surface of said tube member such that when engaging said first ramp and second ramp in moving from said first position to said second position, tension on said lug members and tabs first decreases and then increases.

4. A medical device according to claim 3, wherein:
said outer shield and said inner tube member are of nearly equal length, and said outer surface of said tube member is generally cylindrical and of substantially constant diameter between said first and second ramps; and
said second groove is located substantially at said rear end of said inner tube member, and said first groove is located substantially at the front end of said inner tube member.

5. A medical device according to claim 1, wherein:
said front end of said tube member further comprises a front end wall having an annular opening adapted to have the hollow needle secured thereto, and a hollow neck portion supported by said front end wall, said hollow neck portion extending at least a short distance forward of said front end wall and surrounding said annular opening to form an extension of said annular opening, said neck portion including outwardly extending locking means about an outer surface of said hollow neck portion, and
said front end of said shield member further comprises a front end wall and a circular nozzle supported by said front end wall of said shield member, said circular nozzle forming an extension of said opening in said front end of said shield member for permitting the hollow needle to pass therethrough, and said circular nozzle having inwardly extending locking means located about the inner surface of said circular nozzle and adapted to lock with said outwardly extending locking means to prevent rotational motion of said shield member relative to said tube member when said shield member is in said retracted position.

6. A medical device according to claim 5, wherein:
said outwardly extending locking means comprises a plurality of radially extending ratchet teeth; and
said inwardly extending locking means comprises a plurality of notches for meshing with at least said teeth to prevent rotation of said outer shield relative to said inner tube.

7. A medical device according to claim 6, wherein:
said slots in said rear end of said shield member are coaxial with the longitudinal axis of said shield member and extend a relatively short distance along said shield member; and
said lug members extend circumferentially along the entire circumference transcended by their respective tabs.

8. A medical device according to claim 7, wherein:
said outer surface of said inner tube member is arranged with a first ramp substantially forwardly adjacent said second circumferential groove, said first ramp being of decreasing diameter as it extends forward of said second circumferential groove, and
said outer surface of said inner tube member is further arranged with a second ramp substantially rearwardly adjacent said first circumferential groove, said second ramp being of increasing diameter as it extends forward toward said first circumferential groove, wherein
said lug members are arranged to slidably engage said outer surface of said tube member such that when engaging said first ramp and second ramp in moving from said first position to said second position, tension on said lug members and tabs first decreases and then increases.

9. A medical device according to claim 1, for use with a plunger means and fluid, wherein:
said tube member is adapted to receive the plunger means and the fluid, the plunger means for helping aspirate the fluid through the hollow needle and into said inner tube member and for injecting the fluid out through said inner tube member and the hollow needle.

10. A medical device according to claim 1, for use with a vacuum blood collection vial, wherein the hollow needle is a double ended needle with a first sharp end extending forward said inner tube member, and a second sharp end extending inside said inner tube member, wherein:
said tube member is adapted to receive the vacuum blood collection vial which is pierced by the second sharp end of the hollow needle for collecting a blood sample.

11. A medical device according to claim 1, wherein:
said shoulder includes a ramp having decreasing diameter as it extends forward from said first circumferential groove, said ramp of said shoulder adapted to permitting said lugs of said hollow outer shield member to flex outwardly without destroying the integrity of said outer shield member.

12. In a fluid receiving or dispensing device having a hollow body with a forward and a rearward end and adapted to have a hollow needle secured at said forward end of said hollow body, the needle being of the type which may be used to inject fluids into or withdraw fluids from a body, the inside of said hollow body being substantially cylindrical and sized and shaped to receive therein a rearwardly extending cylindrical plunger or a vacuum blood collection vial whereby a pressure may be produced in the inside of said hollow body or to dispose fluid from the inside of said hollow body, the fluid passing through the hollow needle, the improvement comprising:
a) a substantially cylindrical hollow shield member having a forward and a rearward end and having an inside diameter at least equal to the outside diameter of said cylindrical hollow body and adapted to surround said hollow body, said shield member being slidable from a first position in which said needle is exposed to a second position in which said needle is covered by said shield,
b) a first annular groove on the outer surface of said hollow body, a second annular groove on said outer surface of said hollow body and located more toward said rearward end of said hollow body than said first annular groove, and a shoulder on said outer surface of said hollow body substantially adjacent said first annular groove and located more toward said forward end of said hollow body,
c) a plurality of slits spaced about said rearward end of said shield member, said slits extending forward toward said forward end of said shield member, the portions of said shield member between adjacent slits forming a plurality of slightly flexible tabs, and
d) inwardly extending lug members attached to at least some of said tabs, said lug members being spaced about the rearward end of said shield member, the inner diameter of said lug members being at least as great as the outer diameter of at least most of said outer surface of said hollow body but less than the outer diameter of said hollow body adjacently rearward of said first annular groove, adjacently forward of said second annular groove, and at said shoulder, said lug member engaging said second annular groove to maintain said shield member in said first position and further fixedly engaging said first annular groove to fixedly maintain said shield member in said second position, and in an assembly mode, said lug members engaging said shoulder and flexing outwardly as a result of the engagement, and engaging said outer surface of said hollow body rearward of said first annular groove without fixedly engaging said first annular groove in response to a longitudinal axial movement of said shield member relative to said hollow body.

13. An improved fluid receiving or dispensing device according to claim 12, wherein:

said plurality of slits are coaxial with the shield member circumferentially spaced about said rearward end of said shield member, and extend a short distance toward said forward end of said shield member; and said lug members are integral with said tabs, and each of said lug members extends circumferentially the entire width of said tab member into which it is integral.

14. An improved fluid receiving or dispensing device according to claim 13, wherein:

the diameter of said hollow body gradually decreases from the rearward end of said first annular groove toward the forward end of said second annular groove to form alnog at least a first section of said outer wall of said hollow body a first ramp adapted to slidably engage said lug members.

15. An improved fluid receiving or dispensing device according to claim 14, wherein:

the diameter of said hollow body gradually decreases from the forward end of said second annular groove toward the rearward end of said first annular groove to form along at least a second section of said outer wall of said hollow body a second ramp for slidably engaging said lug members, wherein a third section of said outer wall of said hollow body between said first and second ramp and of decreased diameter relative thereto constitutes a valley between said first and second ramps.

16. An improved fluid receiving or dispensing device according to claim 15, wherein:

said first annular groove is located substantially at the forward end of said hollow body, and said second annular groove is located substantially at the rearward end of said hollow body.

17. An improved fluid receiving or dispensing device according to claim 12, wherein said forward end of said hollow body includes a front end wall having an opening through which the fluid may be received or dispensed, wherein, said forward end of said device includes an axially extending, hollow cylindrical neck portion attached to said front end wall and surrounding said opening to form an extension of said opening in said front end wall, the forward end of said neck portion extending a short distance forward of said end wall and being configured to attach to the hollow needle, the outside surface of said neck portion having outward extending locking means, wherein said hollow shield further includes an end wall having an opening therein and a nozzle forming an extension of said opening in said hollow shield end wall and extending a short distance forward of said shield end wall, said nozzle having an inwardly extending locking means.

18. An improved fluid receiving or dispensing device according to claim 17, wherein:

said inwardly extending locking means comprises notches located circumferentially about the entire inner circumference of said circular nozzle, and said outwardly extending locknig means comprises a plurality of ratchet teeth means adapted to mesh with said notches to prevent rotational motion of said shield member relative to said hollow body when said shield member is in said first position erlative to said hollow body.

19. An improved fluid receiving or dispensing device according to claim 12, wherein:

said shoulder includes a ramp having decreasing diameter as it extends away from said first annular groove, said ramp of said shoulder adapted to permitting said lugs of said hollow shield member to flex outwardly without destroying the integrity of said hollow shield member.

* * * * *